(12) United States Patent
Prus

(10) Patent No.: US 7,652,410 B2
(45) Date of Patent: Jan. 26, 2010

(54) ULTRASOUND TRANSDUCER WITH NON-UNIFORM ELEMENTS

(75) Inventor: Oleg Prus, Haifa (IL)

(73) Assignee: Insightec Ltd, Tirat Carmel (IL)

( * ) Notice: Subject to any disclaimer, the term of this patent is extended or adjusted under 35 U.S.C. 154(b) by 0 days.

(21) Appl. No.: 11/461,763

(22) Filed: Aug. 1, 2006

(65) Prior Publication Data

US 2008/0030104 A1 Feb. 7, 2008

(51) Int. Cl.
*H04R 17/00* (2006.01)

(52) U.S. Cl. .................. 310/334; 310/311; 600/437; 600/459; 367/155

(58) Field of Classification Search ............ 310/334, 310/347, 437, 359; 600/437, 459, 457; 367/157
See application file for complete search history.

(56) References Cited

U.S. PATENT DOCUMENTS

| | | | |
|---|---|---|---|
| 4,052,723 A | | 10/1977 | Miller |
| 5,267,221 A | * | 11/1993 | Miller et al. ............ 367/140 |
| 6,135,971 A | * | 10/2000 | Hutchinson et al. ........ 601/3 |
| 6,503,204 B1 | * | 1/2003 | Sumanaweera et al. ..... 600/459 |
| 6,506,154 B1 | | 1/2003 | Ezion et al. |
| 6,506,171 B1 | | 1/2003 | Vitek et al. |
| 6,582,381 B1 | | 6/2003 | Marantz et al. |
| 6,589,174 B1 | * | 7/2003 | Chopra et al. ............ 600/439 |
| 6,613,004 B1 | | 9/2003 | Vitek et al. |
| 6,618,620 B1 | * | 9/2003 | Freundlich et al. ........ 607/27 |
| 2002/0151790 A1 | | 10/2002 | Abend |

FOREIGN PATENT DOCUMENTS

| | | |
|---|---|---|
| EP | 462311 | 12/1991 |
| FR | 2692999 | 12/1993 |
| GB | 2019565 | 10/1979 |
| WO | WO-9119332 | 12/1991 |

OTHER PUBLICATIONS

International Search Report for PCT Application No. PCT/IB2007/002136 dated Jul. 17, 2008 (4 pages).
Written Opinion for PCT Application No. PCT/IB2007/002136 dated Jul. 17, 2008 (5 pages).

\* cited by examiner

*Primary Examiner*—Walter Benson
*Assistant Examiner*—Bryan P Gordon
(74) *Attorney, Agent, or Firm*—Goodwin Procter LLP

(57) ABSTRACT

An ultrasound transducer comprises a multiplicity of piezoelectric transducer elements attached to a backing layer and forming a two-dimensional array, the transducer elements each comprising one or more piezoelectric members that collectively form an energy transmitting surface of the respective transducer element, the energy transmitting surface having a geometric center, wherein the respective transducer element geometric centers are in an irregular formation.

19 Claims, 12 Drawing Sheets

ULTRASOUND TRANSDUCER WITH NON-UNIFORM ELEMENTS

FIELD OF INVENTION

This application relates generally to multi-element transducers used for delivering high intensity acoustic energy from a multi-element transducer, e.g., a high density, two-dimensional phased-array transducer.

BACKGROUND

It is well-known to use high intensity, focused acoustic wave energy, such as ultrasonic waves (i.e., acoustic waves having a frequency greater than about 20 kilohertz) to generate thermal ablation energy for treating internal body tissue, such as tumors. It is also well-known to employ an imaging system, such as a MRI system, in order to guide the delivery of such high intensity ultrasound energy to the targeted tissue area, and to provide real-time feedback of the actual delivered thermal energy. One such image-guided, focused ultrasound system is the Exablate® 2000 system manufactured and distributed by InSightec Ltd, located in Haifa, Israel (www.InSightec.com).

By way of illustration, FIG. 1 is a simplified schematic representation of an image-guided, focused ultrasound system 100 used to generate and deliver a focused acoustic energy beam 112 to a targeted tissue mass 104 in a patient 110. The system 100 employs an ultrasound transducer 102 that is geometrically shaped and physically positioned relative to the patient 110 in order to focus the ultrasonic energy beam 112 at a three-dimensional focal zone located within the targeted tissue mass 104. The transducer 102 may be substantially rigid, semi-rigid, or substantially flexible, and can be made from a variety of materials, such as plastics, polymers, metals, and alloys. The transducer 102 can be manufactured as a single unit, or alternatively, be assembled from a plurality of components. While the illustrated transducer 102 has a "spherical cap" shape, a variety of other geometric transducer shapes and configurations may be employed to deliver a focused acoustic beam, including linear (planar) configurations. The ultrasound system 100 may further include a coupling membrane (not shown), such as an inflatable body or a balloon filled with degassed water, for providing or improving the acoustic coupling between the transducer 102 and the skin surface of the patient 110.

The transducer 102 may be formed of relatively large number of individually controlled elements 116 mounted on a distal (outward) facing surface 118 (best seen in FIG. 2) of the transducer 102. Each transducer element 116 may itself comprise one or more (adjacent) piezoelectric members electrically connected to a same drive signal supplied from a system controller 106. During operation, the individual piezoelectric members each contribute a fractional part of the ultrasound energy beam 112 by converting the respective electronic drive signal into mechanical motion and resulting wave energy. The wave energy transmitted from the individual piezoelectric members of the transducer elements 116 collectively forms the acoustic energy beam 112, as the respective waves converge at the focal zone in the targeted tissue mass 104. Within the focal zone, the wave energy of the beam 112 is absorbed (i.e., attenuated) by the tissue, thereby generating heat and raising the temperature of the tissue to a point where the cells are denatured ("ablated").

An imager (e.g., an MRI system) 114 is used to generate three-dimensional images of the targeted tissue mass 104 before, during, and after the wave energy is delivered. The images are thermally sensitive so that the actual thermal dosing boundaries (i.e., the geometric boundaries and thermal gradients) of the ablated tissue may be monitored. The location, shape, and intensity of the focal zone of the acoustic beam 112 is determined, at least in part, by the physical arrangement of the transducer elements 116 and the physical positioning of the transducer 102. The location, shape, and intensity of the focal zone may also be controlled, at least in part, by controlling the respective output (e.g., phase and amplitude) of the individual transducer elements 116 by a process known as "electronic steering" of the beam 112. Examples of such physical positioning systems and techniques, and of electronic beam steering, including driving and controlling the output of individual transducer elements, can be found in U.S. Pat. Nos. 6,506,154, 6,506,171, 6,582,381, 6,613,004 and 6,618,620, which are all incorporated by reference herein.

SUMMARY OF THE INVENTION

In accordance with one aspect of the invention, an ultrasound transducer comprising a multiplicity of transducer elements arranged in a two-dimensional array, the transducer elements each comprising one or more piezoelectric members that collectively form an energy transmitting surface of the respective transducer element, the energy transmitting surface having a geometric center, wherein the respective transducer element geometric centers are in an irregular formation. By way of non-limiting examples, the transducer element surfaces may have irregular shapes and/or differing effective lengths. Such differing shapes may be rectilinear, curve-linear, or a combination of each, and may include shapes such as an L-shape, a rectangular shape, a square shape, a T-shape, and an S-shape. The transducer element shapes may be far more complex, similar in appearance as the pieces of an assembled jigsaw puzzle. By constructing the transducer array out of non-uniform (irregular shaped) elements, the resulting geometric centers of the elements are also non-uniform, and the effective range of electronic steering of the transducer may be increased over that of a conventional transducer array having uniform-shaped energy transmitting element surfaces, without formation of potentially harmful and energy depleting hot spots.

Other and further aspects and features of various embodiments of the invention will become evident from the following detailed description and accompanying figures.

BRIEF DESCRIPTION OF THE DRAWINGS

FIG. 8 is a top view of a two-dimensional array of transducer elements having irregular shaped energy transmitting surfaces, in accordance with one embodiment of the invention.

DETAILED DESCRIPTION

High density ultrasound transducers have been developed in which the transducer is produced in the form of a two-dimensional grid of uniformly shaped piezoelectric (PZT) "rods" glued to a conductive matching layer substrate. For both manufacturing and performance reasons, the PZT rods have rectangular (or square) profiles, with an aspect ratio (i.e., ratio of height/width) of greater than or equal to one, and are preferably uniform in size to produce the same frequency response. Spacing between the rods also influences the acoustic performance of the transducer and is preferably minimized, i.e., much smaller than the size of the individual piezoelectric rods, for therapeutic transducers. A high density phased array transducer may have hundreds, even thousands of densely packed piezoelectric rods, each having a relatively small energy transmitting surface, e.g., 1 mm square.

Figure 1:
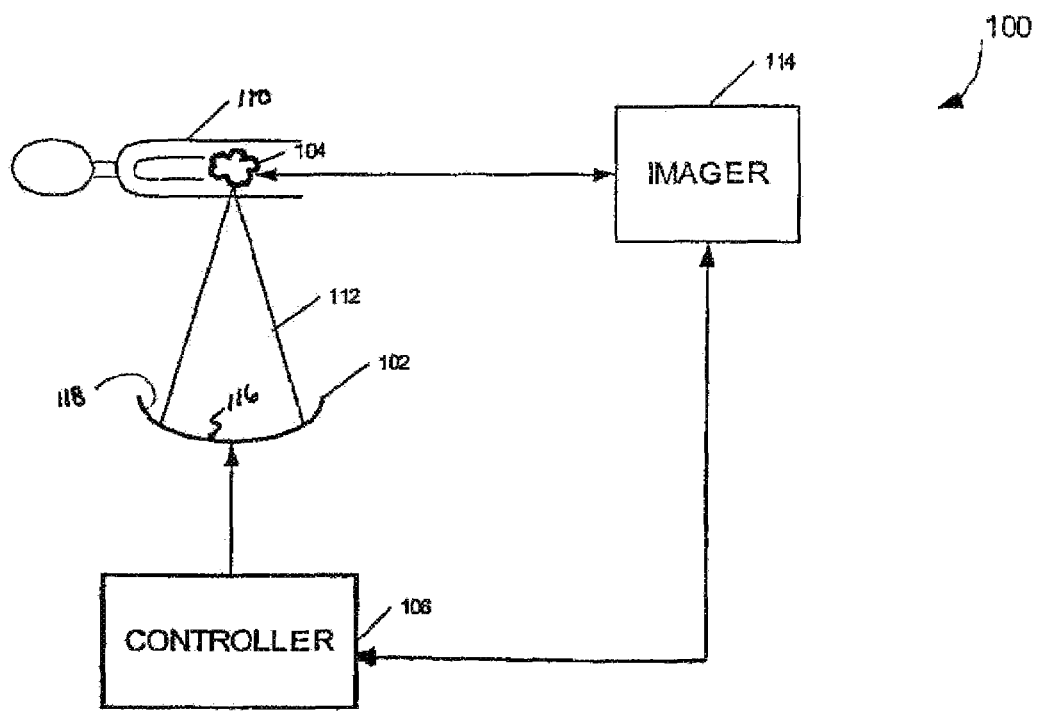
FIG. 1 is simplified schematic diagram of an image-guided focused ultrasound treatment system for providing thermal energy dosing of a targeted tissue region in a patient.
Figure 2:
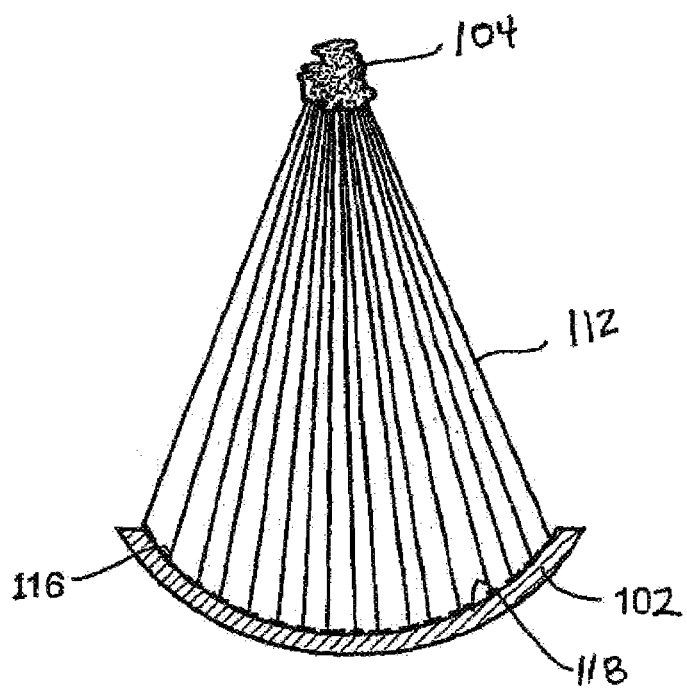
FIG. 2 is a cut-away schematic side view of the ultrasound transducer used in the system of FIG. 1, illustrating a concentrated emission of focused ultrasonic energy originated from a multiplicity of individual elements to a focal zone in the targeted tissue region.
Figure 3:
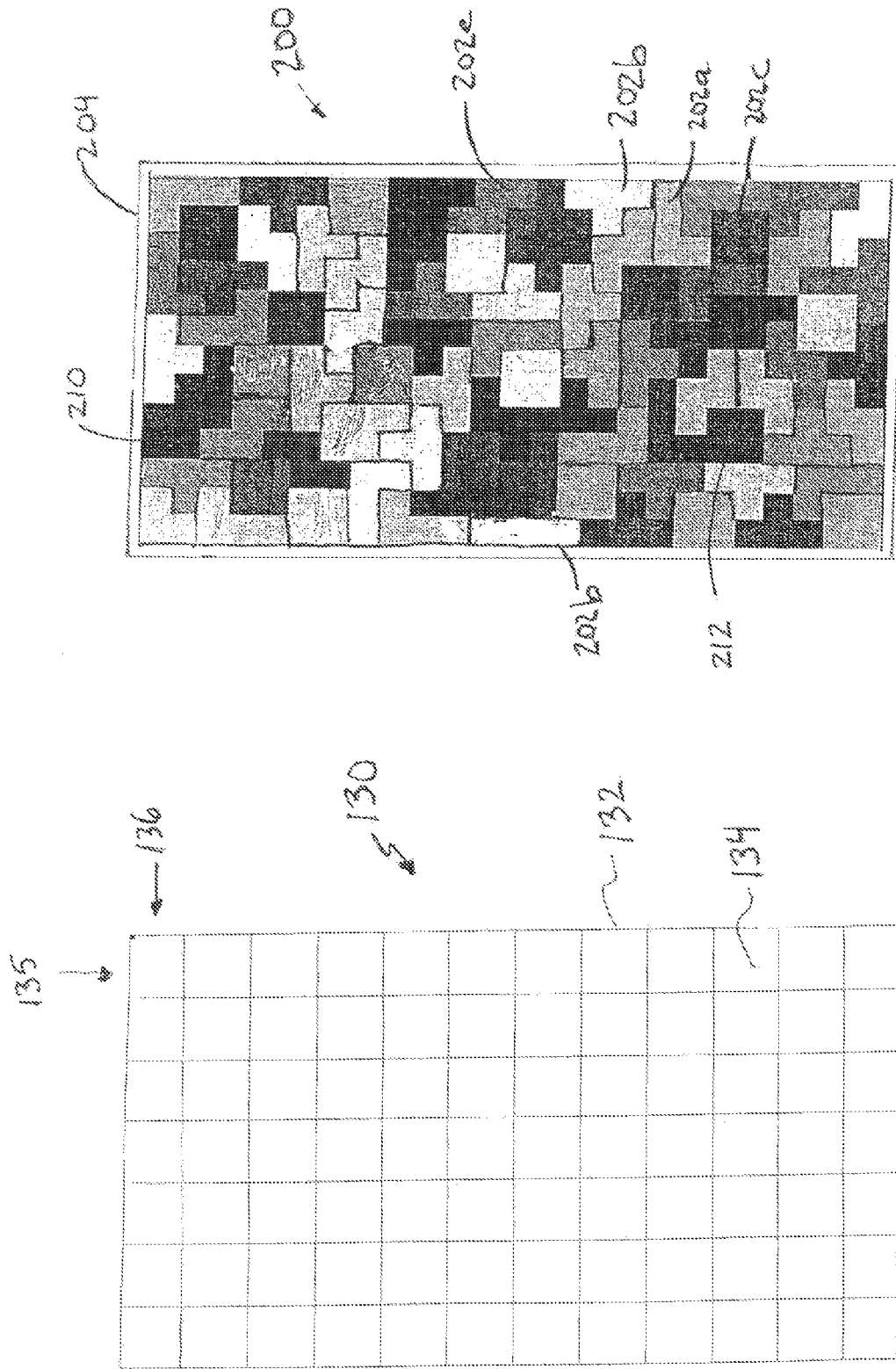
FIG. 3 is a top view of a conventional two-dimensional array of transducer elements having uniform (rectangular) energy transmitting surfaces.

An example of one such high density transducer array 130 of uniformly shaped piezoelectric rods is shown in FIG. 3. The transducer array 130 comprises a two-dimensional arrangement of individual piezoelectric rods 132 glued to a planar substrate. The piezoelectric rods 132 are substantially identical in size and shape, including having substantially uniform (square) distal facing energy transmitting surfaces 134 (also square). The rods 132 are arranged in uniformly aligned columns 135 and rows 136, with minimal spacing provided between adjacent rods. It will be appreciated that the relatively small transducer rod size allows for greater electronic steering capability of the overall array. However, as the "steering angle" increases, hot spots start to appear outside of the intended focal zone.

More particularly, the independent piezoelectric rods 132 in such known arrays 130 are typically produced using a dicing machine that can dice along straight lines only. Each rod is connected to its own electronic drive signal input, such that each rod forms a distinct transducer element. From a physical point of view, the acoustic performance (e.g., frequency response, efficiency, etc) of the array 130 is influenced by the three dimensional structure of the individual rods 132, and preferably each rod's height should be equal or higher than its width. However, the steering/focusing ability of the transducer array 130 is fully defined by the geometrical surface (i.e., the area of a transducer element that emits a respective acoustic wave at a same phase) of the respective rods 132. All internal transducer structure aspects, such as piezoelectric rod height, aspect ratio, etc, are irrelevant to steering/focusing ability.

As used herein, the term "hot spot" refers to a tissue region having an energy level (which may be measured, for example, in terms of temperature or acoustic pressure) that is above a prescribed (safe) level at which the tissue in the hot spot will be temporarily or permanently injured. Because such hot spot(s) start to appear as the electronic steering angle increases, electronic steering to each possible "steered-to" focal zone must be carefully analyzed for safety purposes before undertaken. Further, the energy absorbed at the hot spot(s) decreases the remaining energy available for contributing to the intended "steered-to" focal zone.

Figure 4:
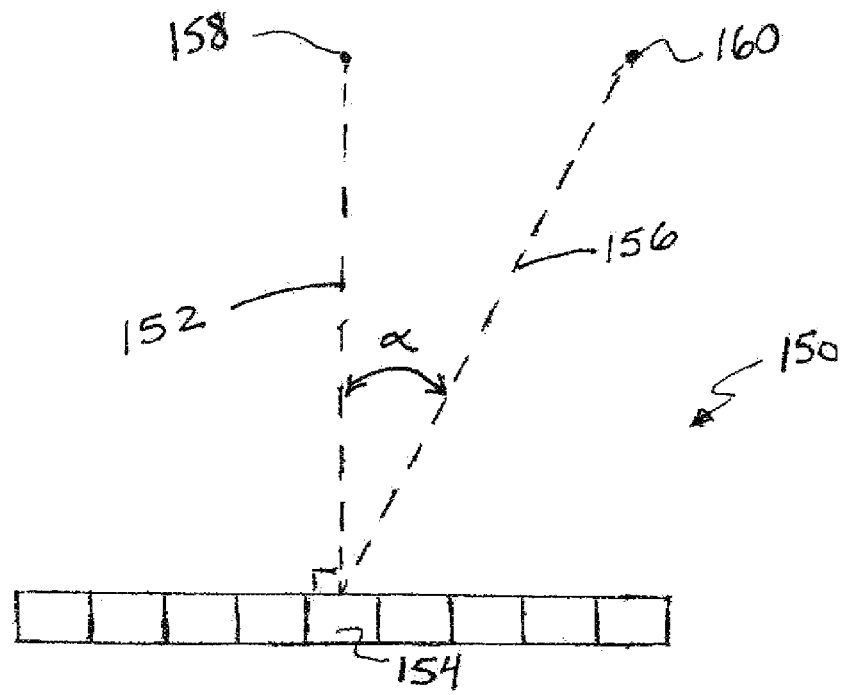
FIG. 4 illustrates the principle of electronic steering, and a resulting "steering angle" when transmitting to a "steered-to" focal zone using with a uniform transducer array.

FIG. 4 illustrates the principle of electronic steering of a two dimensional planar array 150 comprised of uniformly shaped and arranged elements (such as array 130 of FIG. 3). In particular, the "steering angle" of any one transducer element 154 of the array 150 is the angle α formed between a first focal axis 152 extending generally orthogonally from the element to a "non-steered" focal zone 158 at which the element 154 contributes a maximum possible power, and a second focal axis 156 extending from the transducer element 154 to a "steered-to" focal zone 160. The "steering ability" of the transducer array 150 is defined as a steering angle α at which energy delivered to the steered-to focal zone 160 from a given one-dimensional element row falls to half of the maximum power delivered to the non-steered focal zone 158.

Figure 6:
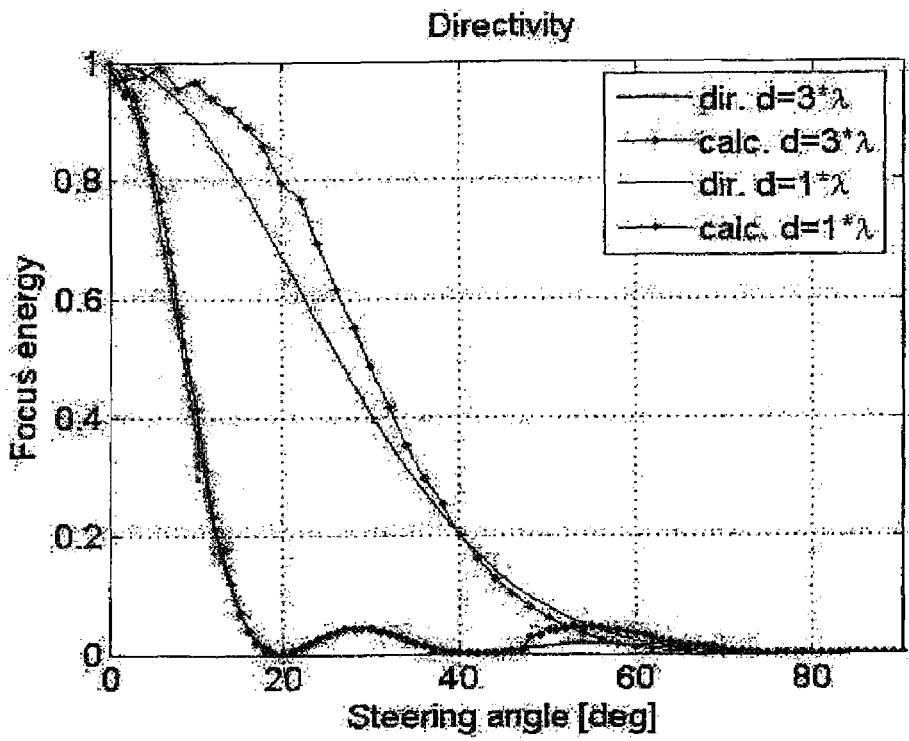
FIG. 6 is a chart depicting the relationship between the "directivity" of a transducer element of the array and an energy flux calculation in Fourier space for differently sized transducer elements, 1λ and 3λ.
Figure 7:
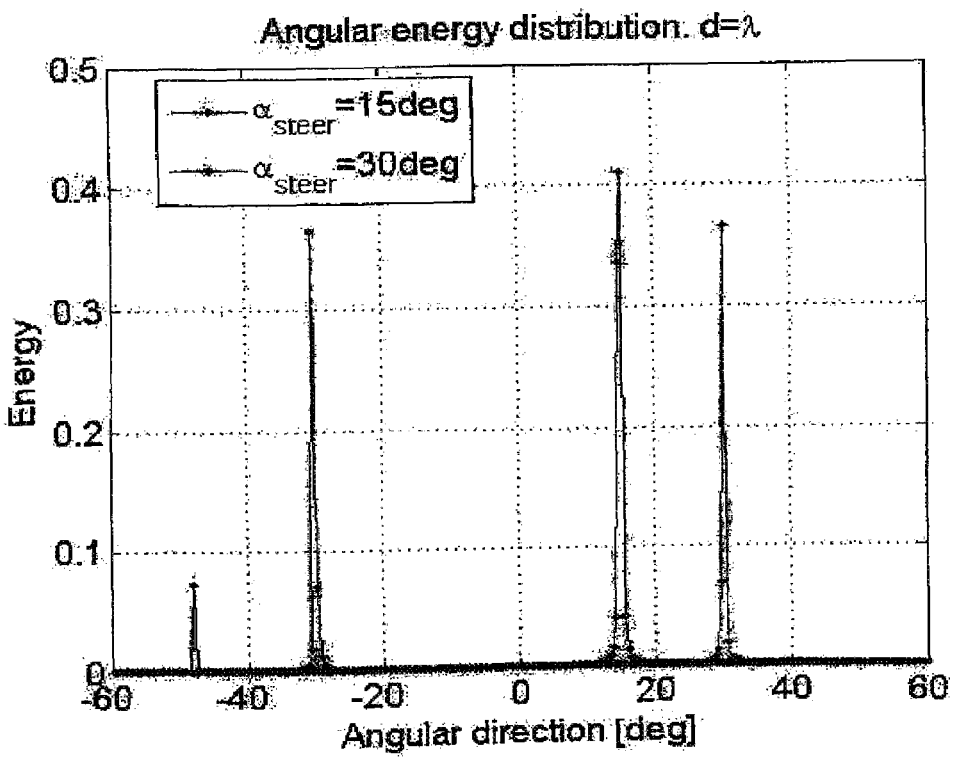
FIG. 7 is a comparison of hot spots created by electronic steering from linearly arranged transducer elements having a size d=λ to respective 15° and 30° steering angles.

Notably, the steering angle if each transducer element of a phased array will be different. However, as the distance to a steered-to focal zone increases, the respective steering angles for the array elements approach the same value. For ease in illustration, the distance of the steered-to focal zone in the simulations in FIGS. 5-7 is assumed to be infinity, so that the steering angles of each array element is the same.

From a physical point of view, a single transducer element emits a wave in the form of a spreading beam. The angular distribution of this spreading beam is called "directivity." While a single element of an array (if it is the only element that is activated), cannot produce a focused beam, an array of activated elements can produce focused beam, where the size of the "focus" is smaller when transducer elements have larger emitting surface areas. Each transducer element contributes to the focus proportionally to the value of its directivity at the "focus." Thus, the steering region of a phased array transducer is dependent on each element's directivity patterns.

Figure 5:
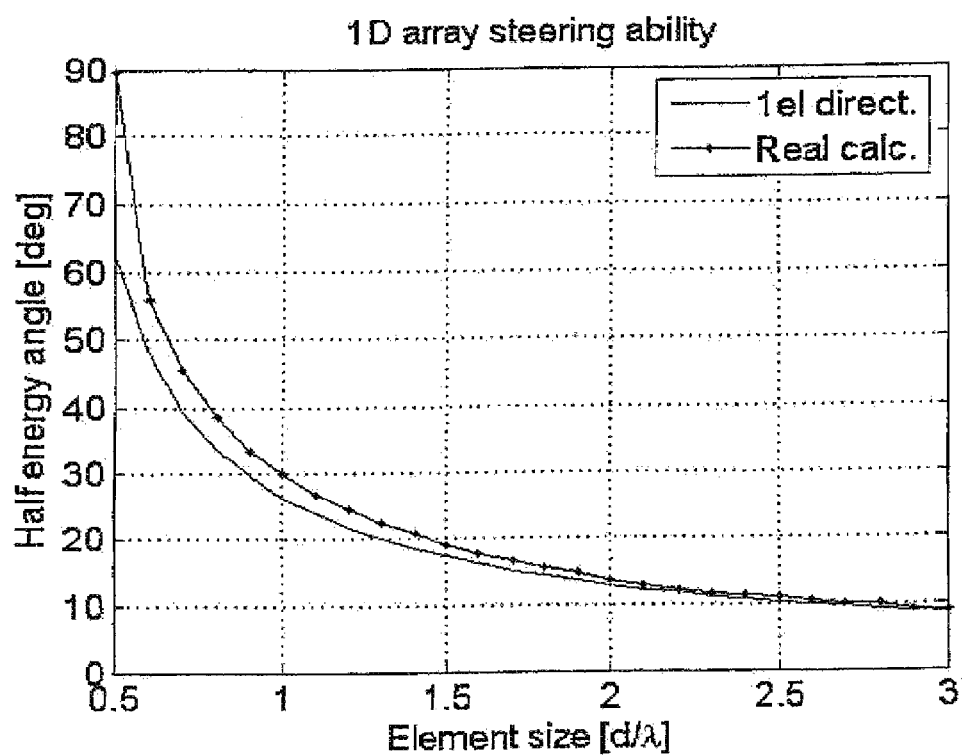
FIG. 5 is a graph plotting the half energy or "steering ability" of a transducer element of the array, based on its size.

By way of further illustration, FIG. 5 depicts the relationship between a transducer element surface size and its steering ability, represented in terms of its half-energy angle. For purposes of illustration, there are two curves shown in FIG. 5. There are two curves shown in FIG. 5; one (labeled "1 el direct") is a simplified analytical result of the element's directivity; the other (labeled "real calc") is a numerical simulation for a phased array transducer. As can be seen, for a transducer element having a size d/λ, where λ is the wavelength of the wave emitted by the element, the half energy steering angle, or "steering ability," of the transducer array with d/λ=1 is 30°, which is the angle at which a steered-to focal zone has an energy level equal to half the maximum energy that the transducer would contribute to a non-steered focal zone.

In order to better illustrate the relationship between the electronic steering angle and formation of hot spot(s), consider a one-dimensional array (i.e., row) of transducer elements having a cross sectional dimension (i.e., element surface size) of $d/\lambda=1$. If $\Delta\phi$ is a phase difference between neighboring elements of the array, maximum energy emission occurs at angles satisfying the relationship: $\sin(\alpha)=(n+\Delta\phi/2\pi)\lambda/d$, where $\lambda$ is an ultrasound wavelength, integer $n=0$ for the main focus and $n\neq0$ for hot spots. Thus, where $d\leq\lambda/2$, no hot spots will be formed. As such, the advantages of the embodiments described below particularly apply where the element size is equal to or greater than one-half of the drive signal wavelength.

The electronic steering ability of a transducer device can be defined by:

$$I_s \equiv \frac{\text{Energy at main focus}}{\text{All emmited energy}}.$$

For $d \gg \lambda$, the steering ability approaches single element "directivity,"

$$I_d = \left(\frac{\sin(\pi d \sin(\alpha)/\lambda)}{\pi d \sin(\alpha)/\lambda}\right)^2.$$

FIG. 6 shows a comparison of this directivity formula to energy flux calculation in Fourier space for two different ultrasound wavelengths, $1\lambda$ and $3\lambda$.

As a result of the hot spot generation, large steering angles cannot be practically used, since nearly all of the energy that does not go to the steered-to focal zone is concentrated at hot spots. As can be seen in FIG. 7, for $d=\lambda$, while attempting to steer to 30°, hot spots are produced at −30° of equal intensity as the main focus, reducing the steering ability that can be safely used to about half of the main focus steering ability. It will be appreciated by those skilled in the art, that as the steering angle amplitude (absolute value) increases, hot spots begin to appear at numerous different points, and are both uncontrollable and undesirable.

In accordance with a general aspect of the invention, a high density, two-dimensional transducer array is formed using transducer elements having irregular shaped energy transmitting surfaces. In various embodiments, the transducer element surface shapes may have rectilinear or curve-linear profiles, or a combination of both, and may include many different types of "irregular" shapes. By way of example, a multi-element transducer array 200 constructed according to one embodiment of the invention is shown in FIG. 8. In particular, the multi-element array 200 comprises irregular shaped transducer elements 202 having at least five different element shapes, including an L-shape 202a, a rectangular (or "I") shape 202b, a square shape 202c, a T-shape 202d, and an S-shape 202f, respectively, which are mounted to a substrate 204 in an interlocking (or mating) configuration, resembling a "Tetris" game formation.

Figure 8A:
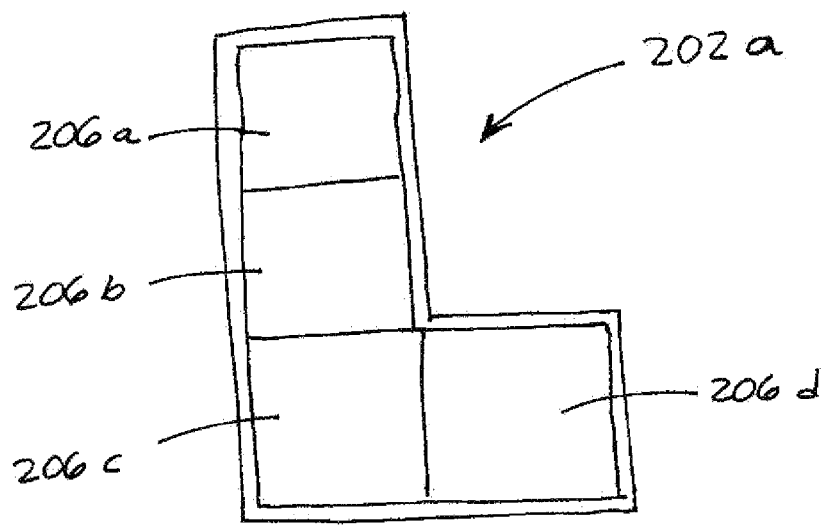
FIGS. 8A and 8B illustrate one technique for forming the non-uniform transducer elements in the array of FIG. 8.
Figure 8B:
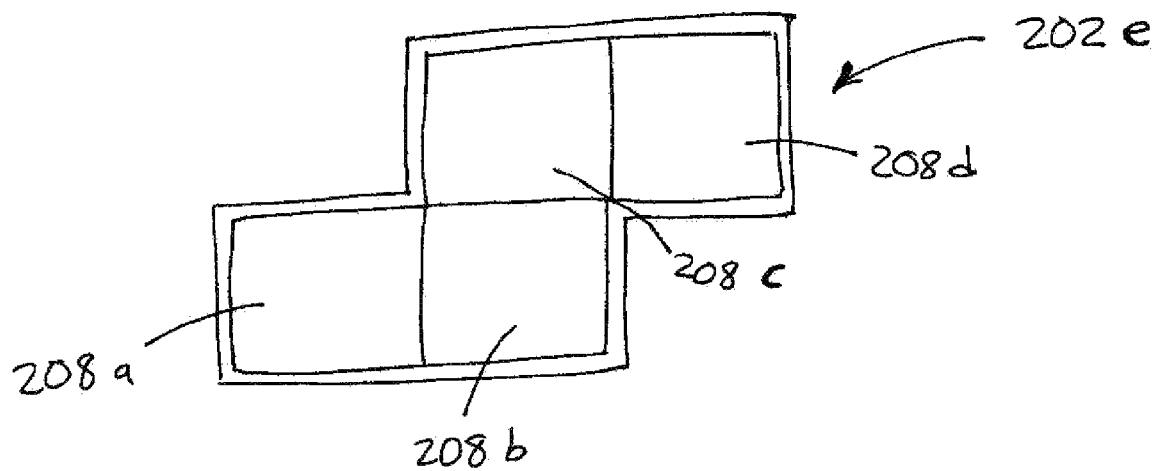

The array 200 may be constructed, by way of example and not limitation, using a conventional dicing machine, but making much smaller cuts to create a uniform array of piezoelectric rods in the same formation as shown in FIG. 3. However, the individual rods are then coupled to a same electronic drive signal in order to form the irregular shaped elements 202 of the array 200. For example, as shown in FIG. 8A, an L-shape element 202a may comprise three adjacent and aligned square rods 206a-c, along with a forth rod 206d located adjacent to the third rod 206c and orthogonal to the alignment of rods 206a-c. Similarly, as shown in FIG. 8B, an S-shape element 202e may be formed by electrically coupling four square rods 208a-d in an S-shape formation. It should be appreciated, however, that the transducer elements 202 may also be formed by one-piece piezoelectric elements, instead of a mosaic arrangement of smaller component elements.

Figure 9:
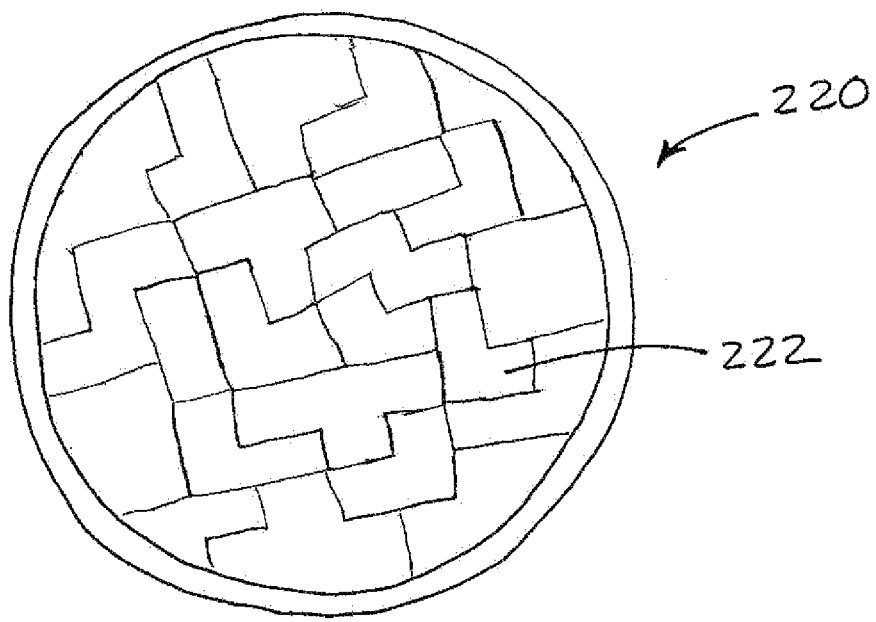
FIG. 9 is a top view of another two-dimensional array of transducer elements having irregular shaped energy transmitting surfaces, in accordance with another embodiment of the invention.
Figure 10B:
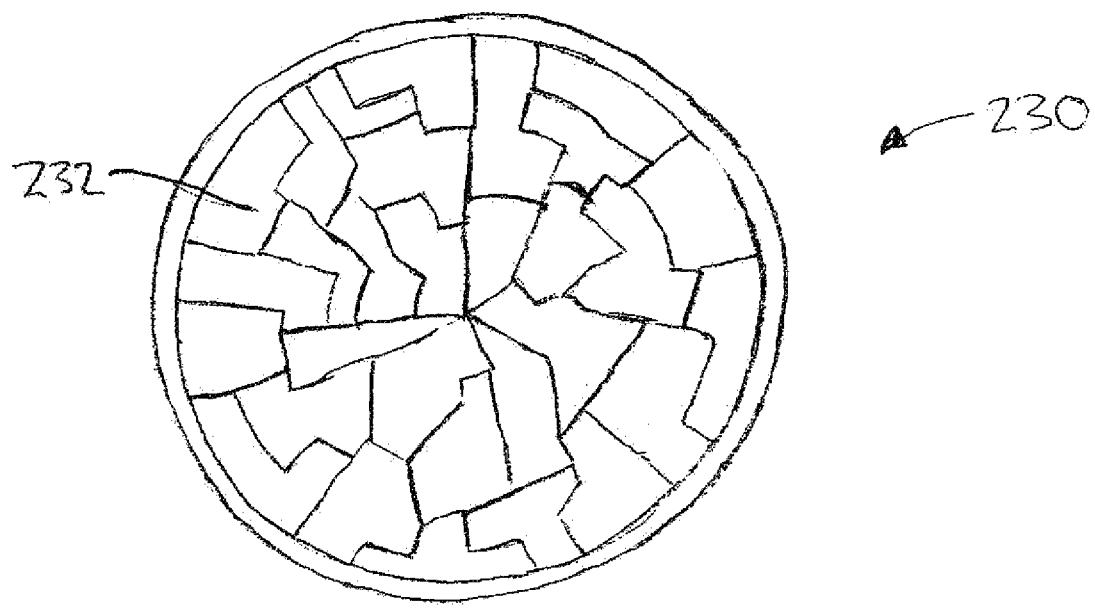
FIGS. 10A and 10B are top views of further two-dimensional transducer arrays having irregular shaped energy transmitting elements, in accordance with yet further embodiments of the invention.
Figure 10A:
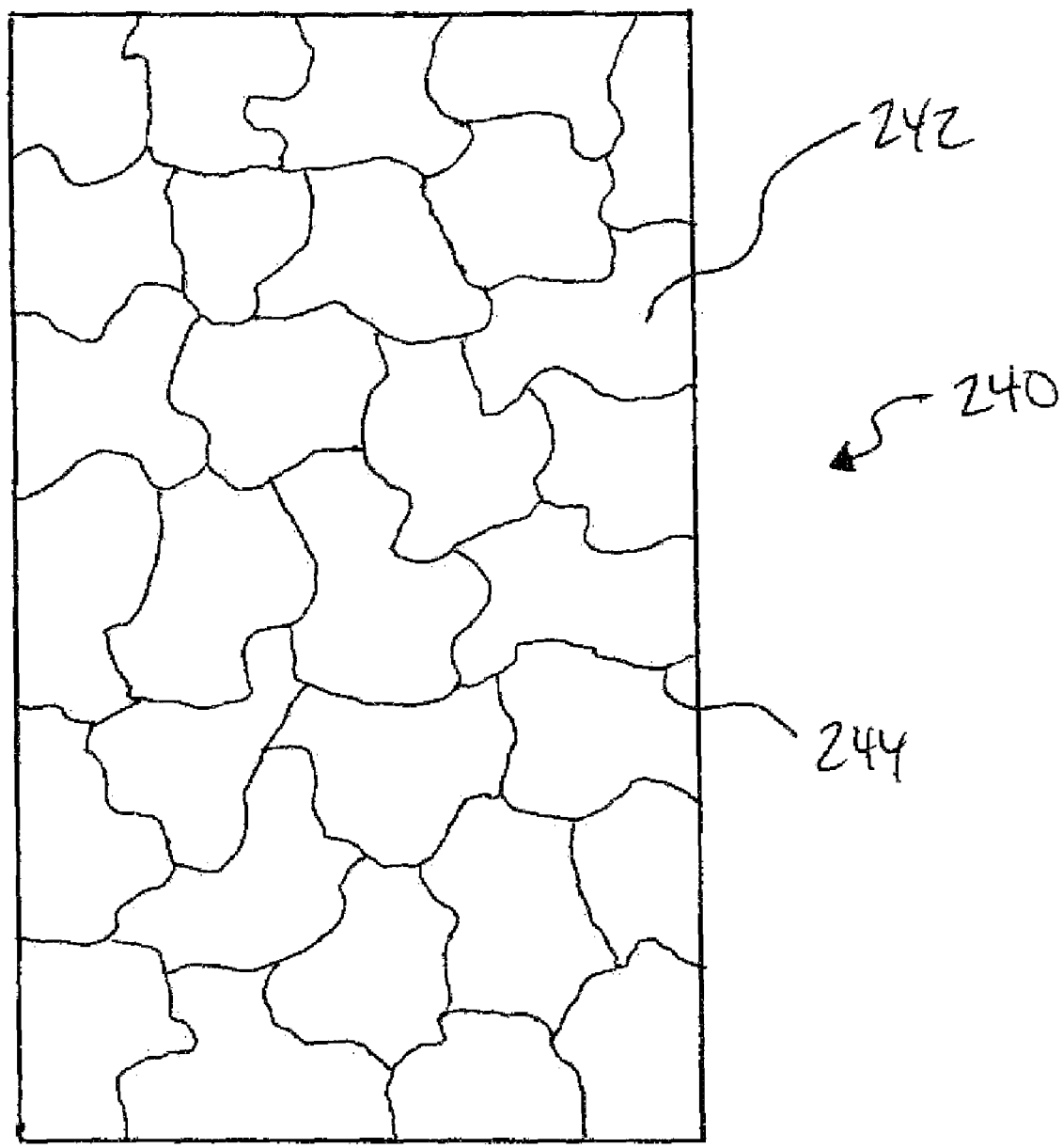

While the array 200 of FIG. 8 has a generally planer configuration, it is possible for such irregular shaped transducer arrays to employ other configurations. For example, a spherical cap transducer array 220 having irregular ("Tetris") shaped elements 222 is shown in FIG. 9. Moreover, the "Tetris" shapes of FIGS. 8 and 9 are but two examples of transducer arrays having non-uniform transducer elements. Multi-element arrays 240 and 230 having more complex, pseudo random shaped elements 242 and 232, respectively, are shown in FIGS. 10A and 10B. Notably, the elements 242 and 232 have curve-linear profiles instead of the rectilinear profiles of elements 202 and 222 of arrays 200 and 220, respectively.

In the various embodiments contemplated by the invention, the irregular shaped elements of a transducer array preferably have the same or similar total surface areas, e.g., with each element being formed by connecting a same number of smaller piezoelectric elements in differing patterns. However, it is acceptable that some elements of the transducer array have differing surface areas, (such as elements 210 and 212 in array 200, which may be formed out of five, instead of four, square rods). Although the surface areas of the respective elements of an array may differ, they will still respond to the same frequency, while possibly producing slightly different amplitudes (depending on whether any compensation is made to the drive signal current, which is spread over a lesser or greater surface area).

Further, it will be appreciated that the elimination of hot spots in embodiments of the present invention is due to the non-uniform locations of the geometric centers of the respective transducer elements 202. In particular, the geometrical "centers" of neighboring elements 202 of the array are randomly shifted by the length of the element comparable with its size (e.g., anywhere from a ratio of 1/4 to a ratio of 1/1). In contrast, in a conventional "uniform" transducer arrays the geometric centers of the elements are "ordered" along straight lines or circles. In a therapeutic focused ultrasound system, it is desirable to deliver maximal energy delivery to the focal zone and minimal energy to any other locations. This is normally achieved by maximal transducer area coverage by emitting elements.

Thus, in embodiments of the present invention, "random order" may be obtained while retaining full area coverage by emitting elements by using "irregular shaped" and/or "irregular oriented" transducer elements. While this results is some "smearing" of the acoustic waves and, thus, some (relatively small) corresponding loss of energy intensity at the focal zone, the steering capability of the respective array greatly exceeds that of a conventional uniform-shaped transducer array of otherwise similar element size. In particular, the appearance of hot spots is greatly decreased by the element disorder of an irregular shaped array, while the main focal zone has only a minor power degradation. Further, the element size may be much larger than the acoustic wavelengths that are used. Many different irregular shape patterns are possible within the ambit of the invention, with the particular element pattern realized on the substrate specifically chosen depending on the particular steering angles to be achieved without the formation of prohibitive hot spots. Because of the disorder in the waves caused by the irregular element shapes and positions, only the main focus survives. The use of an irregular shaped array for improved electronic steering when delivering therapeutic levels of ultrasound energy is fundamentally different from a (known) "parsing" technique used for ultrasound imaging, in which gaps (uniform or varied) between elements are used to increase steering performance. While a similar effect may be achieved by irregular spacing of the elements, this would result in large gaps and unacceptable losses in output power in the case of a therapeutic transducer application. Further, the gaps between elements causes more spreading in space of the acoustic energy for the same focal zone power delivery, which in turn may cause excessive heating of the surrounding tissue.

The effect of the reduction in hot spots and the benefit of using the irregular shaped transducer array 200 of FIG. 8 versus the uniform-shaped transducer array 130 of FIG. 3 may be demonstrated with reference to FIGS. 11A-B, 12A-B, 13A-B, 14A-B and 15A-B. In particular, images generated by 3-D simulations of respective converging acoustic energy beams transmitted from a multi-element transducer having uniform-shaped elements is shown in FIGS. 11A, 12A, 13A, 14A and 15A, and images generated by 3-D simulations of respective converging acoustic energy beams transmitted from a multi-element transducer having irregular shaped elements are shown in corresponding FIGS. 11B, 12B, 13B, 14B and 15B). Each of the pictures represents an acoustic pressure field obtained by the respective transducer array at the same conditions. Each field was obtained by phasing the transducer to obtain a maximum power at the desired focus position measure in x, y, x distances from the transducer array.

Figure 11A:
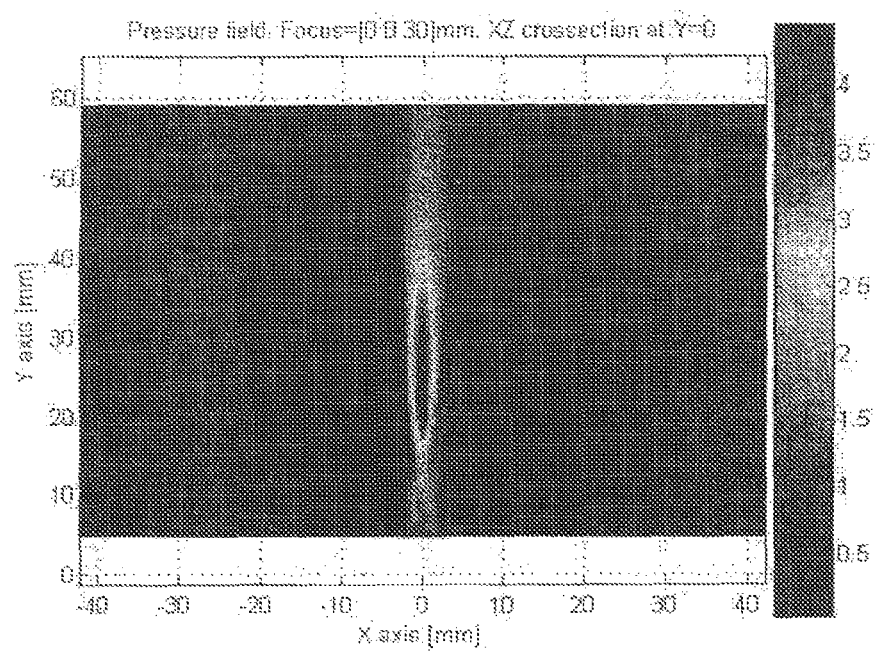
FIGS. 11A-B, 12A-B, 13A-B, 14A-B and 15A-B are images generated by 3-D simulations of respective converging acoustic energy beams transmitted from a multi-element transducer having uniform-shaped elements (FIGS. 11A, 12A, 13A, 14A and 15A), or irregular shaped elements (FIGS. 11B, 12B, 13B, 14B and 15B).
Figure 11B:
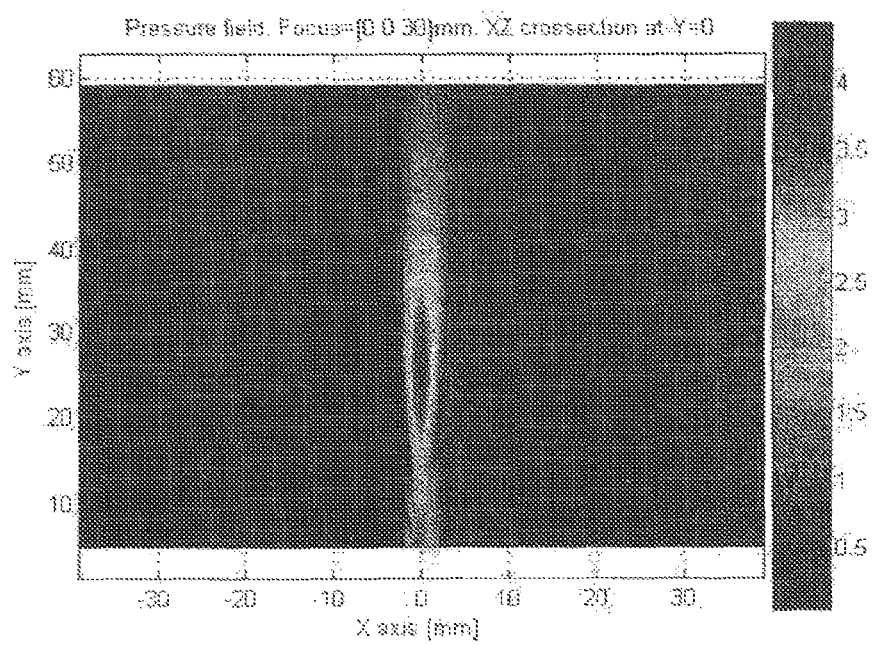
Figure 12A:
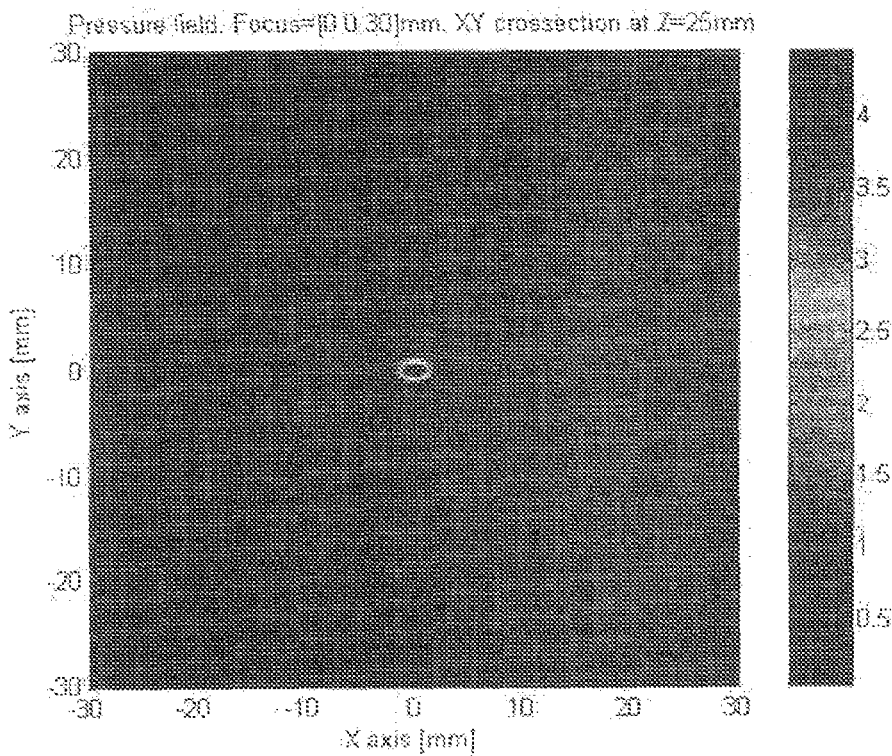
Figure 12B:
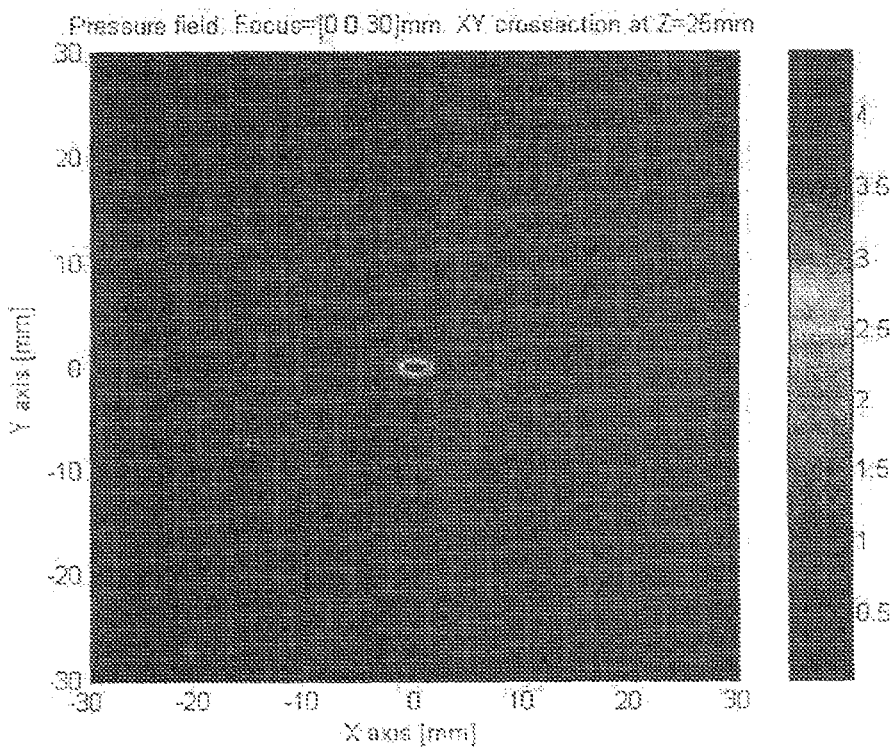
Figure 13A:
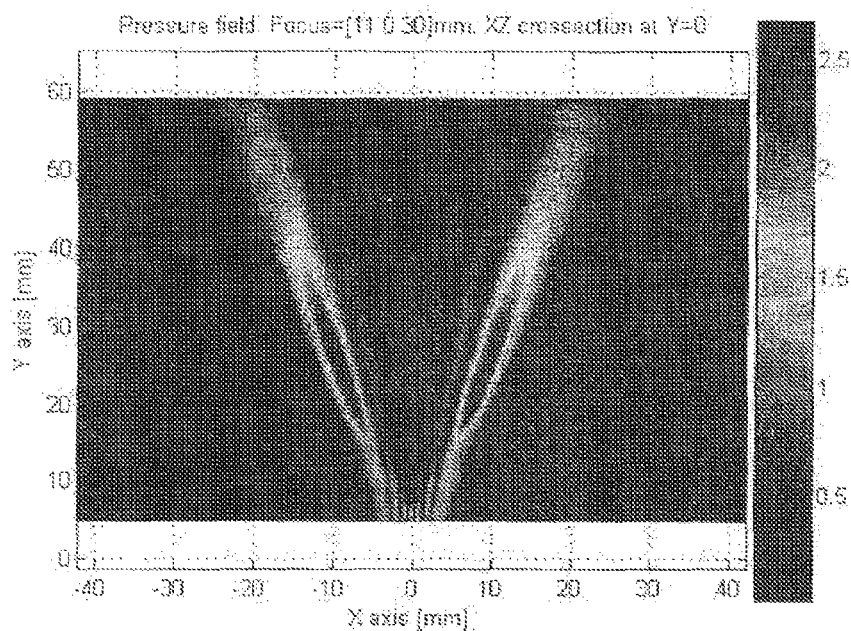
Figure 13B:
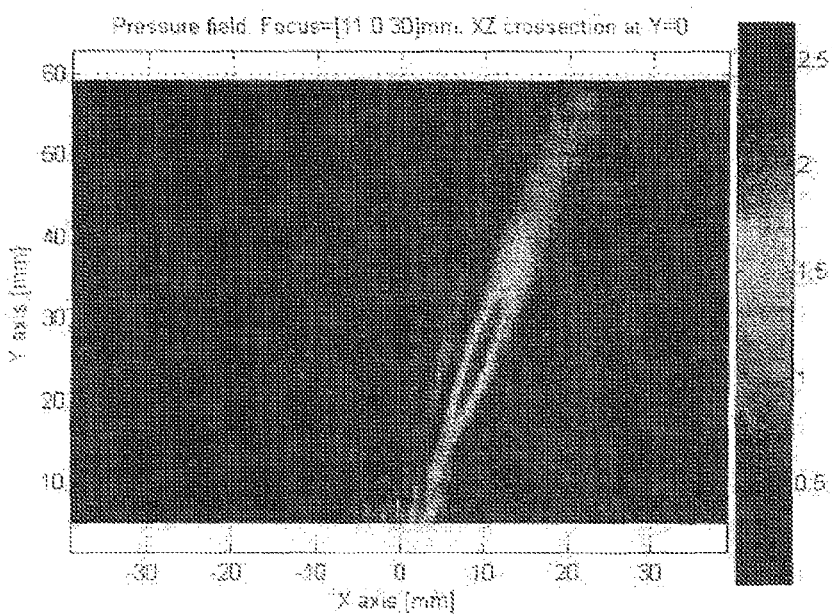
Figure 14A:
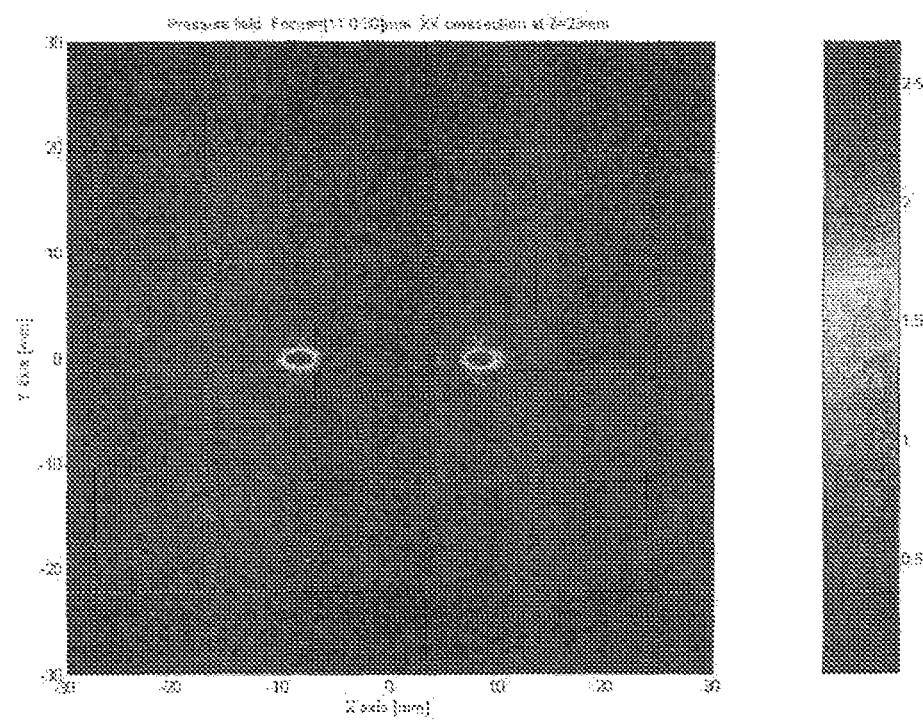
Figure 14B:
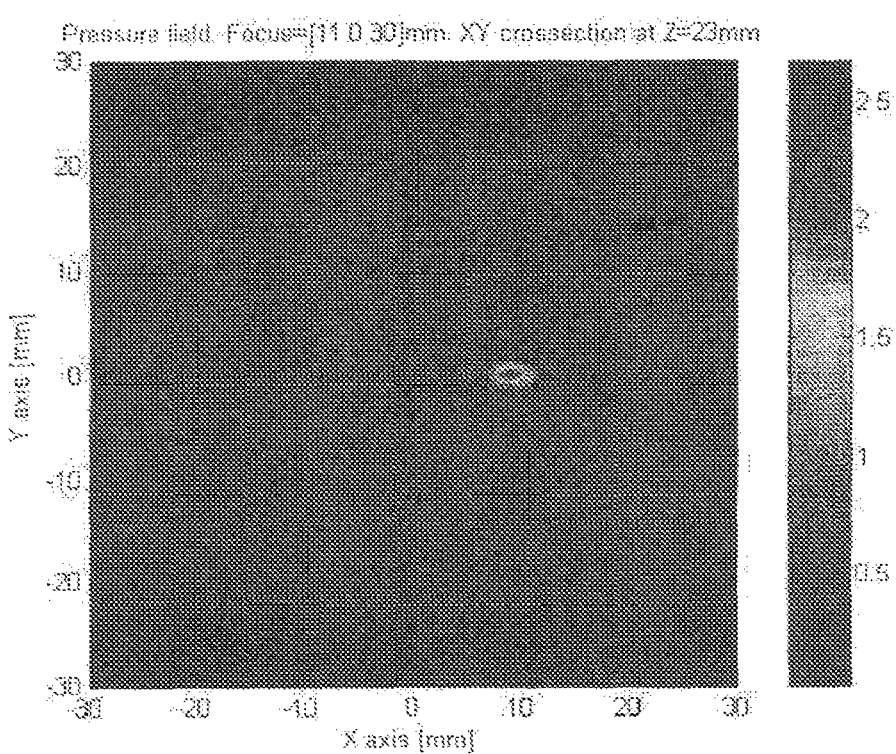

FIGS. 11A and 11B are the respective acoustic pressure fields at the x, y, z coordinates of 0, 0, 30 mm (i.e., taken along the z-axis with zero electronic steering). As can be observed, the pressure fields are very similar, with the field in 11B (from the irregular shaped elements) being a slightly "reduced amplitude" version of the field generated by the uniform-shaped elements shown in FIG. 11A. FIGS. 12A and 12B show the respective x-y cross-section of the fields shown in FIGS. 11A and 11B, for z=25 mm. FIGS. 13A and 13B are the respective acoustic pressure fields at the x, y, z coordinates of 11 mm, 0, 30 mm, i.e., with an electronic steering angle out of the x-pane of 20.1°. As can be seen, the field generated by the uniform-shaped elements (FIG. 13A) has a significant hot spot reduction formed at 20.1° (−11 mm, 0, 30 mm) in the x-plane. FIGS. 14A and 14B show the respective x-y cross-sections of the fields shown in FIGS. 13A and 13B, for z=23 mm.

Figure 15A:
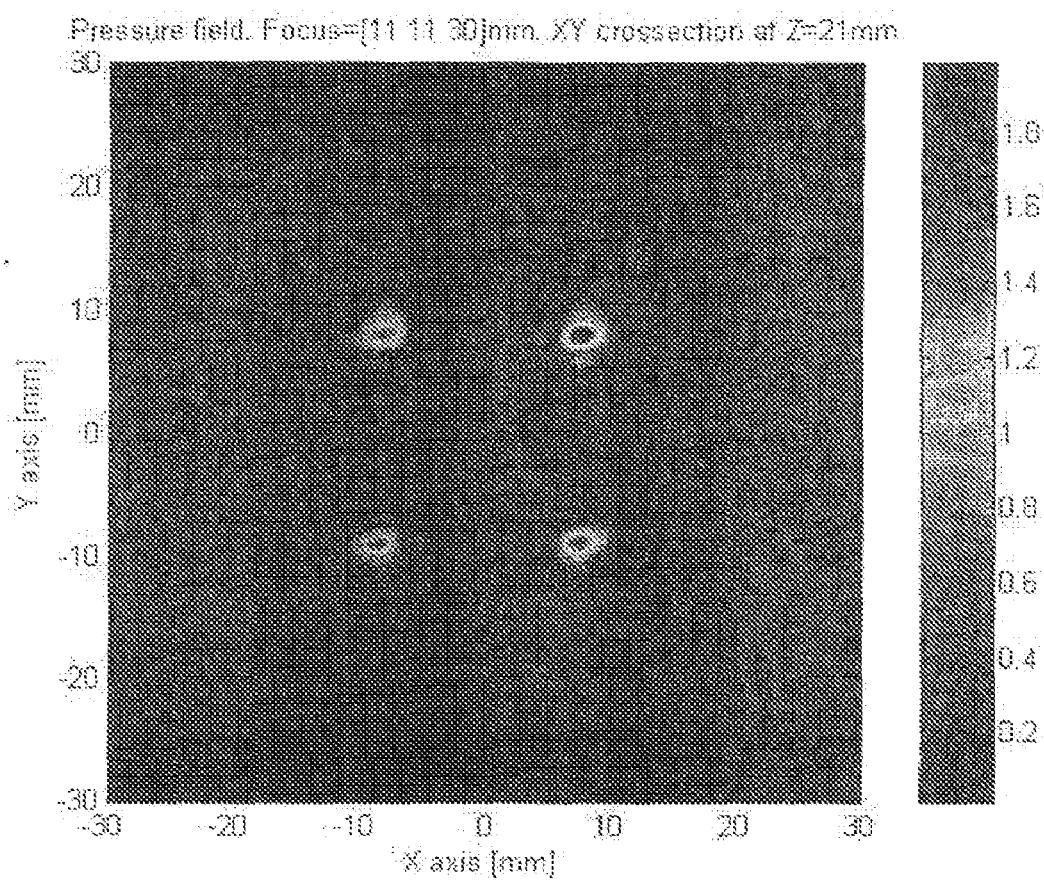
Figure 15B:
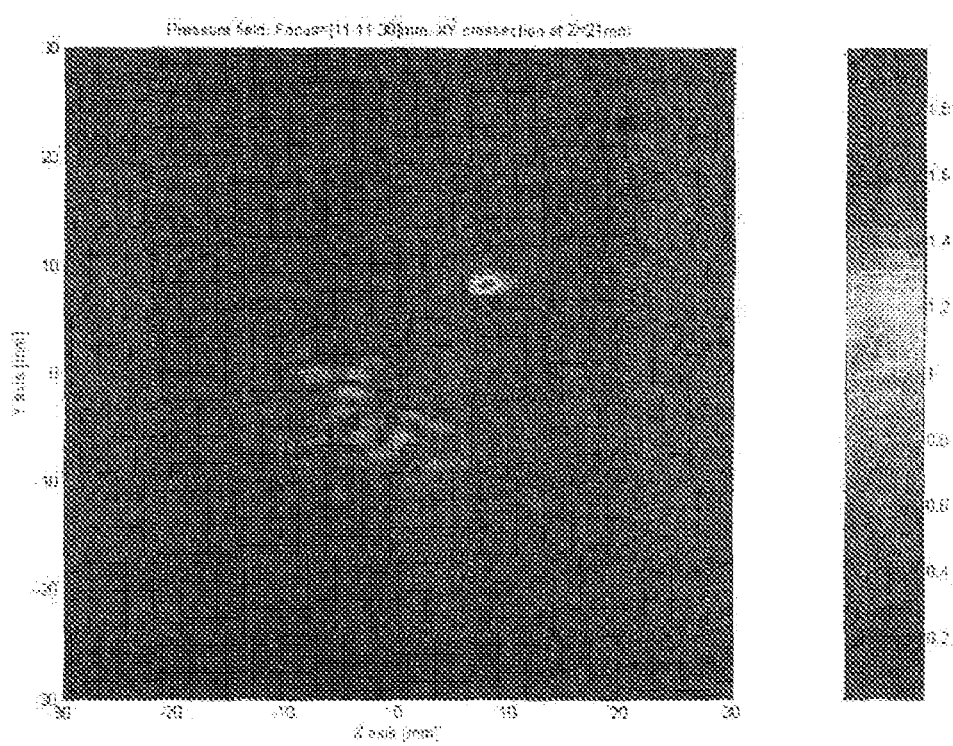

FIGS. 15A and 15B are taken at respective x-y cross-sections (for z=21 mm) of acoustic pressure energy fields having x, y, z coordinates of 11 mm, 11 mm, 30 mm, i.e., with an out-of-plane steering angle of 27.4° in both the x and y directions. As can be seen in FIG. 15A, electronic steering to this focal zone using a conventional, uniform-shaped transducer array results in hot spots at each of the "mirror-image" locations, i.e., at coordinates (−11 mm, 11 mm, 30 mm), (11 mm, −11 mm, 30 mm), and (−11 mm, −11 mm, 30 mm). On the other hand, as can be seen in FIG. 15B, by using a transducer array having irregular shaped elements, there are no distinct hot spots such as seen in FIG. 15A, even though there is an energy increase throughout the cross-sectional plane.

In some embodiments, before the respective transducer array is activated to deliver treatment-level ultrasound energy, an acoustic wave simulation can be performed to determine if any hot spots will be generated. For example, a computer model of the transducer may be created to model the configuration (e.g., shape, size, and relative position) of the transducer elements. Various operational parameters (such as operation frequencies, amplitudes, and operation phases for the respective transducer elements) can then be applied to the computer model to determine if a hot spot will result from a certain operational condition. As will be appreciated by those skilled in the art, while all transducer elements of an array may be activated in some instances, e.g., in order to maximize an amount of energy delivered to a steered-to focal zone, in other instances, sufficient therapeutic energy may be delivered without activating all elements of the array. Also, while the above embodiments have been described with reference to creating a single focal zone, in other embodiments, the same or similar methods can be used to create a plurality of simultaneous focal zones, thereby allowing simultaneous treatment of multiple target tissue regions.

Thus, although particular embodiments of the invention have been shown and described, it should be understood that the above discussion is not intended to limit the invention to these illustrated and described embodiments, which are provided for purposes of example only. Instead, the invention is defined and limited only in accordance with the following claims.

What is claimed is:

1. An ultrasound transducer, comprising:
   a two-dimensional array comprising a plurality of transducer elements, each transducer element (i) comprising a grouping of piezoelectric members, (ii) wherein elements in each grouping receive the same input signal and (iii) having a geometric center, such that the grouped piezoelectric members form a single energy transmitting surface of the respective transducer element, and wherein the geometric centers are arranged in an irregular formation.

2. The ultrasound transducer of claim 1, wherein transducer elements of the array have irregularly shaped energy transmitting surfaces.

3. The ultrasound transducer of claim 2, wherein the transmitting surfaces have shapes including at least one of an L-shape, a rectangular shape, a T-shape, or an S-shape.

4. The ultrasound transducer of claim 2, wherein the transducer elements of the array are arranged in an interlocking configuration.

5. The ultrasound transducer of claim 2, wherein the piezoelectric members have rectilinear profiles.

6. The ultrasound transducer of claim 2, wherein the piezoelectric members have curvilinear profiles.

7. The ultrasound transducer of claim 1, wherein the transducer is an imaging transducer.

8. The ultrasound transducer of claim 1, wherein the transducer is a therapeutic energy transducer.

9. The ultrasound transducer of claim 1, wherein adjacent transducer elements of the array have respective energy transmitting surfaces with different shapes.

10. The ultrasound transducer of claim 1, wherein three or more transducer elements having different surface lengths form a row of the array such that the distance between the geometric centers of any two transducer elements of the row is different than the distance between the geometric centers of any other two transducer elements the row.

11. An ultrasound transducer, comprising:
    a two-dimensional array of non-uniformly shaped transducer elements, each transducer element comprising a grouping of substantially uniform piezoelectric members coupled to a single input signal and which collectively form a single energy transmitting surface of the respective transducer element.

12. The ultrasound transducer of claim 11, wherein the non-uniformly shapes comprise at least one of an L-shape, a rectangular shape, a T-shape, and an S-shape.

13. The ultrasound transducer of claim 11, wherein the elements are arranged in an interlocking configuration.

14. The ultrasound transducer of claim 11, wherein the piezoelectric members have rectilinear profiles.

15. The ultrasound transducer of claim 11, wherein the piezoelectric members have substantially same surface areas.

16. The ultrasound transducer of claim 11, wherein the transducer is an imaging transducer.

17. The ultrasound transducer of claim 11, wherein the transducer is a therapeutic energy transducer.

18. A high density ultrasound transducer configured for delivering therapeutic energy for heating body tissue, the transducer comprising:

a two-dimensional array comprising a plurality of transducer elements, each transducer element (i) comprising a grouping of piezoelectric members, (ii) wherein the elements in each grouping receive the same a single input signal and (iii) having a geometric center, the piezoelectric members forming a single energy transmitting surface of the respective transducer element, wherein:

the transducer elements of the array have irregularly shaped energy transmitting surfaces such that the geometric centers are arranged in an irregular formation, and the transducer elements of the array are arranged in an interlocking configuration.

19. The ultrasound transducer of claim 11, wherein the groups are arranged in an interlocking configuration.

* * * * *